United States Patent [19]

Blanchard

[11] 4,002,428
[45] Jan. 11, 1977

[54] DEDUCTIVE METHOD FOR MEASURING ION CONCENTRATION ELECTRICALLY

[75] Inventor: Carl L. Blanchard, Stone Mountain, Ga.

[73] Assignee: The United States of America as represented by the Secretary of the Interior, Washington, D.C.

[22] Filed: May 21, 1976

[21] Appl. No.: 688,657

[52] U.S. Cl. .................. 23/230 R; 324/30 R
[51] Int. Cl.² ............. G01N 27/00; G01N 31/02
[58] Field of Search ........... 324/30 R; 23/232 E, 23/253 R, 230 A, 230 R; 204/195 R, 195 F, 195 G

[56] References Cited

UNITED STATES PATENTS

| | | | |
|---|---|---|---|
| 2,880,071 | 3/1959 | Gelman | 23/232 E |
| 3,591,481 | 7/1971 | Riseman | 204/195 R |
| 3,880,722 | 4/1975 | Beltzer | 23/232 E |

Primary Examiner—Rudolph V. Rolinec
Assistant Examiner—Michael J. Tokar
Attorney, Agent, or Firm—William S. Brown; Donald R. Fraser

[57] ABSTRACT

A deductive analytical method, using measurements of specific conductivity and pH, for determining the concentration of a desired ion in a sample which may contain multiple ionic species without removal of the ions from solution is disclosed. The method involves the steps of: measuring the specific conductivity and the pH of the sample and of a reagent; adding an excess of the reagent capable of reacting with the desired ion, e.g. causing precipitation, thereby reducing the specific conductivity of the sample; measuring the pH and specific conductivity of the sample-reagent mixture; comparing the pH and specific conductivity values of the sample, the reagent and the reaction product of the sample and reagent; and deducing the concentration of the measured ion from these values by calculation. This method permits measurement of an ionic species by a simple rapid technique which utilizes measurements on simple equipment and avoids the more complex and time-consuming operations of separation and weighing used in the prior art.

8 Claims, No Drawings

DEDUCTIVE METHOD FOR MEASURING ION CONCENTRATION ELECTRICALLY

BACKGROUND OF THE INVENTION

1. Field of the Invention

This invention relates to a method for determining the concentration of specific ions in solution. More specifically the invention provides a method of making determinations of ionic concentrations solely by electrical measurements of specific conductivity and pH without any necessity of removing ions from solution.

2. Description of the Prior Art

A number of methods are already known in the art for measuring the concentration or specific ions in solution. For example, the traditional methods employed in quantitative analysis are suitable. One such method involves the introduction into the sample solution of a reagent which is capable of forming a precipitate with the ion whose concentration is to be measured. The precipitate is separated from the solution, dried, weighed, and then the amount of the ion of interest is calculated based on the amount of precipitate formed. This method is cumbersome and time consuming and requires essentially non-portable equipment such as accurate weighing apparatus and an oven. Moreover, the method requires some skill on the part of the operator.

It is also known that the determination of the concentration of many ions can be made by the use of commercially available potentiometric electro-chemical electrodes. Such electrodes yield a continuous-signal output voltage having a simple logarithmic relation to ion activity, and a sufficiently fast response. This logarithmic relation is the well-known Nernst equation. However, the output voltage which is observed is not necessarily simply related to concentration for a number of reasons. First, the activity of a given ion in a solution is affected by the background activity of other ions, i.e., the total ionic strength of the solution. As the strength of the latter increases, generally one expect that the activity of a given ion apparently decreases. Also, often ions are complex and in such a case, the measured activity differs markedly from the concentration. For example, an electrode sensitive to fluoride ion activity simply does not given an accurate measurement of the fluoride concentration, for example in sea water where there is an excess of magnesium ion present because fluoride can be complexed by magnesium.

It is desirable in many instances to show the concentration of a species of ions in solution rather than its activity. A method and an apparatus for this purpose is disclosed in U.S. Pat. No. 3,591,481 issued July 6, 1971 to Rieseman. In this method concentration measurements are effected by relating the electrode potential resulting from an unknown or sample solution with the electrode potential from a mixture of that sample solution with a standard solution of known concentration of the ion of interest or a strong complexing or precipitating agent for the ion of interest. The method of obtaining a measurement requires two essential steps. First, the electrode sensitive to the ion of interest is immersed into a specific volume (e.g., 50 ml.) of the sample solution containing an unknown amount of the ion of interest; the potential developed then causes a deflection of a meter movement in accordance with the Nernst equation. The meter movement is then adjusted to a null point and a small known volume (e.g., 1 ml.) of a standard solution containing a known concentration of the ion of interest (or a strong complexing or precipitating agent therefor) is added to the sample. The addition of the standard solution will change the total so that a new potential will arise which causes the meter movement to deflect away from the null point by some value $\Delta E$. Since the concentration of the standard solution is predetermined, the concentration of the sample will appear as a reading on the meter scale or base expressed typically in moles per liter based on the value of $\Delta E$.

The method of this invention provides an alternative to the method in the foregoing patent and differs essentially therefrom in that an excess of the complexing or precipitating agent in the standard (reagent) solution is used, that the concentration of the complexing or precipitating agent need not be predetermined and that the measurements made are of pH and specific conductivity rather than electrode potential as in the reference.

SUMMARY OF THE INVENTION

The essential principle of this invention is based on the fact that electrical conductivity of solutions is proportional to the number and type of ions present. Conductivity due to only one type of ion may be determined if the ion is selectively removed from the solution or if the ion is made non-conductive by its precipitation or by binding it into an essentially non-conductive complex. The sample in which the desired ion has been "neutralized" by making it non-conductive has its conductivity decreased by an amount that is due to the number of the desired ions which have been "neutralized".

The quantitative determination of the concentration of the desired ion requires that the initial conductivities of the sample solution and the reagent solution be known and that the final conductivity of the mixture of the sample and reagent solution be measured. In its simplest aspect the measurement of concentration depends on the comparison of the conductivity which would be expected for a mixture of the sample and reagent solutions assuming no precipitation or complexing reaction took place with the actual measured conductivity which is lower because a precipitation or complexing reaction does necessarily take place.

Briefly, the process of this invention comprises the following steps:

a. measuring the pH and specific conductivity of the sample solution and of a reagent solution;

b. adding and reacting a measured excess amount of the reagent solution of a known constitution to the measured amount of sample solution, the reagent solution being selected so that it is capable of reacting with the desired ion to give a substantially non-ionic product without substantial reaction taking place between the reagent solution and the other ions in solution;

c. measuring the pH and specific conductivity of the mixture obtained in step (b);

d. mathematically deducing the concentration of the desired ion by comparing the specific conductivity expected in a mixture of the sample solution and the reagent solution, assuming no reaction had taken place, with the measured specific conductivity for the solution obtained in (b) and by making any necessary corrections for pH changes and for the solubility of the product of reaction between the desired ion and the reagent solution.

In the example below the method of this invention is illustrated by measuring the sulfate ion concentration of a sample solution containing a number of ions. The reagent solution is barium chloride which, as well known, precipitates sulfate ion as barium sulfate which is highly insoluble. It is evident that the method illustrated in the example can be adapted to measure the concentration of other ions in solution by selection of an appropriate reagent which will precipitate or complex with the desired ion to give a substantially non-ionic complex. Any number of reagents suitable for precipitation of certain ions from solution are well known from classical quantitative analysis. For example, silver nitrate can be used to precipitate, and therefore measure the concentration of, halide ion in solution. Similarly, the desired ion can be bound in a complex compound which is substantially non-ionic. The nature of the precipitate or complex and its formation is not part of this invention inasmuch as suitable precipitates and complexes are well-known in the art.

The considerations involved in formation of the precipitate or complex are similar to those involved in classical quantitative analysis in which the desired ion is removed as a precipitate, for example, and is weighed. For instance, the pH of the sample may require adjustment in order to assure an environment in which the precipitate is insoluble or solubility is minimized, or for other reasons. Also, the reagent used to form the precipitate or complex obviously must be in excess in order to assure complete reaction of the desired ion. To this extent, the concentration of the reagent must be known approximately and the concentration of the desired ion must also be known within a certain order or magnitude. It is further essential that the rate of the chemical reaction between the reagent and the desired ion be considered in order to allow sufficient time for complete reaction before final reading of conductivity.

While the method of this invention is operative over a wide range of concentrations it must be recognized that salt effects may have to be considered when the method is used at higher conductivities and that super saturation may cause apparent failure of the method. Therefore, it is preferred that the sample and reagent be present in relatively low concentrations which may require dilution of the sample or reagent. It is preferred that sample and reagent be diluted or chosen to give specific conductivity readings in the range of less than 1,000 micromhos. Inaccuracy due to coprecipitation may occur but is minimized and is not very likely at low concentration and low ranges of conductivity.

As indicated above, corrections may be necessary in the concentration value which is calculated from a comparison of the specific conductivity of the reaction product between the sample solution and the reagent and the specific conductivity which would be expected had no reaction occured when the sample and reagent were mixed. Specifically, large changes in pH require correction based on conductivity for hydrogen ion. It also may be important to make correction for solubility of the reaction product, i.e. the precipitate or complex. The calculations involved in determining concentrations of the desired ion from the measured specific conductivity and pH at various stages are relatively simple and can be easily made manually. However, large scale use of the analytical method of this invention would benefit by computer processing.

The invention is illustrated by the following example which is intended to show one actual embodiment utilizing the principle of this invention but which is not intended to limit the invention in any way. Variations on the example utilizing the same principle will be apparent to those skilled in the art.

EXAMPLE

This example illustrates the use of the method of this invention for the measurement of the concentration of sulfate ion in an aqueous solution containing a number of other ionic species.

A reference sample was submitted to a number of laboratories for determination of sulfate ion concentration. The average reported value was 20.5 mg/l. In addition to sulfate the reference sample contained the following ions:

$SiO_2$, Ca, Mg, Na, K, $HCO_3$, Cl, F, and $NO_3$.

The same reference sample above was analyzed for sulfate content by the method of this invention in which the following steps were followed:

1. The specific conductivity and pH of the sample were measured. The specific conductivity was 107 micromhos and the pH was 7.4 (The pH of the sample must be below 8.2).

2. Reagent of analytical grade barium chloride was prepared by adding the chemical to deionized water and mechanically stirring. Water was added to adjust the specific conductance to about 250 micromhos. The specific conductance was measured and the final value of 256 micromohos recorded. the pH was measured as 5.9 and recorded.

3. An aliquot of 100 milliliters of the sample was pippetted into a 250ml beaker containing a magnetic stirring bar to which 50 milliliters of barium chloride reagent was added. Mechanical stirring of the mixture started.

4. A projected zero reference specific conductance was determined by the weighted average of the conductance of the sample and reagent. 2(107)+256=470 micromhos X.333=156.67 micromhos.

5. Final measurement of the specific conductance and pH were made after one hour. The final specific conductance of 118 micromhos and pH 6.7 were recorded. 6. The final specific conductance of the solution was subtracted from the zero point specific conductance. 156.67 micromhos-118 micromhos=38.67 micromhos.

7. The net specific conductance of 38.67 micromhos was multiplied by 1.5 to return the sample to unit volume or a condition wherein only the sample volume is considered. The net was 58.0 micromhos, at unit volume.

8. The net specific conductance found in step 7 was corrected for changes in the hydrogen ion concentration. First the change in hydrogen ion concentration of the barium chloride solution in going from its original pH of 5.7 to the final pH of 6.7 was calculated. Next, the change in hydrogen ion concentration of the reference sample in going from its original pH of 7.4 to the final pH of 6.7 was calculated as an equivalent change in the anion concentration. The values obtained were converted to conductance units. These values were summed and the result, 0.22 micromhos, was subtracted from the net specific conductance of 58.0 micromhos.

9. The net conductivity of the barium sulfate (from the chemical reaction) was divided by the empirically corrected constant of 142 micromhos/meq (1/2 BaSO$_4$ equivalent conductance).

10. The 0.406 meq of barium sulfate was multiplied by 48.032 mg/meq sulfate to determine the uncorrected sulfate concentration of 19.5 mg/l.

11. The sulfate fraction of the known solubility of barium sulfate was added to the determined concentration 19.5 mg/l + 1.5 mg/l sulfate = 21.0 mg/l sulfate.

The calculated value of 21. mg/l of sulfate compares well with the value of 20.5 (above) obtained by averaging values obtained by a number of laboratories.

We claim:

1. A method for measuring the concentration of a desired ion in a sample solution containing multiple ionic species without removing ions from solution comprising the steps of:
   a. measuring the pH and specific conductivity of the sample solution and of a reagent solution;
   b. adding and reacting a measured excess amount of said reagent solution of known constitution to a measured amount of sample solution wherein said reagent solution is capable of reacting with the desired ion to give a substantially non-ionic product without substantial reaction with other ions in solution;
   c. measuring the pH and specific conductivity of the mixture obtained in step (b);
   d. mathematically deducing the concentration of the desired ion by comparing the specific conductivity expected in a mixture of the sample solution and the reagent solution, assuming no reaction had taken place, with the measured specific conductivity for the solution obtained in (b) and by making any necessary corrections for pH changes and corrections for the solubility product of reaction between the desired ion and the reagent solution.

2. The method of claim 1 wherein the reagent solution is capable of forming a precipitate with said desired ion.

3. The method of claim 1 wherein said reagent is capable of forming a substantially non-ionic complex with said desired ion.

4. The method of claim 1 in which said sample solution contains a multiplicity of anions and the desired ion is an anion.

5. The method of claim 1 in which said sample solution contains a multiplicity of cations and said desired ion is a cation.

6. The method of claim 1 in which sample and reagent volumes are such that all specific conductivity readings are below 1000 micromhos.

7. The method of claim 1 in which said sample solution contains a multiplicity of anions including sulfate which is the desired ion and said reagent solution comprises an aqueous solution of a water soluble barium salt.

8. The method of claim 1 in which the step of mathematically deducing concentration of the desired ion is conducted by computer.

* * * * *